(12) United States Patent
Vail

(10) Patent No.: US 6,517,275 B2
(45) Date of Patent: Feb. 11, 2003

(54) NEEDLE TUBE LOCK FOR TATTOO MACHINES

(76) Inventor: Walter H. Vail, 2734 W. Highland St., Chandler, AZ (US) 85224

( * ) Notice: Subject to any disclaimer, the term of this patent is extended or adjusted under 35 U.S.C. 154(b) by 0 days.

(21) Appl. No.: 09/761,900

(22) Filed: Jan. 17, 2001

(65) Prior Publication Data

US 2002/0094229 A1 Jul. 18, 2002

(51) Int. Cl.[7] ................................................. B25G 3/30
(52) U.S. Cl. ..................... 403/88; 403/89; 403/109.4; 403/377
(58) Field of Search ..................... 403/88, 89, 84, 403/109.4, 377

(56) References Cited

U.S. PATENT DOCUMENTS

| | | | | |
|---|---|---|---|---|
| 46,458 A | * | 2/1865 | Flanders .................... | 403/88 |
| 374,052 A | * | 11/1887 | Fisher ....................... | 403/88 |
| 1,724,812 A | * | 8/1929 | Waters ...................... | 81/9.22 |
| 2,346,364 A | * | 4/1944 | Dowe ........................ | 403/88 |
| 2,588,623 A | * | 3/1952 | Eliscu et al. ................ | 81/9.22 |
| 4,159,659 A | * | 7/1979 | Nightingale ................ | 81/9.22 |
| 4,931,059 A | * | 6/1990 | Markham .................. | 606/185 |
| 4,970,976 A | * | 11/1990 | Kitai et al. ................. | 112/162 |
| 6,162,195 A | * | 12/2000 | Igo et al. ................... | 604/164 |

* cited by examiner

Primary Examiner—Lynne H. Browne
Assistant Examiner—Kenn Thompson
(74) Attorney, Agent, or Firm—Gregory J. Nelson

(57) ABSTRACT

A needle tube lock for a tattoo machine. The lock has a clamp arm which receives a threaded fastener and a needle tube arm which has a bore which receives the needle tab. The arms are integrally formed from stainless steel or other suitable sterilizable material. The lock is positioned about the needle tube and may be rotated relative to the needle tube retainer to a selected position and secured by tightening the fastener against the retainer. In this way, the tattoo machine is usable even if the retainer is broken or damaged.

2 Claims, 1 Drawing Sheet

NEEDLE TUBE LOCK FOR TATTOO MACHINES

FIELD OF THE INVENTION

The present invention relates to tattoo machines and more particularly relates to a universal locking device for securing a needle tube to a tattoo machine.

BACKGROUND OF THE INVENTION

Tattooing is an ancient art which has become very popular in recent years. Tattooing is practiced by professional tattoo artists using a tattoo machine. The basic design of a tattoo machine has remained basically unchanged for a number of years. The tattoo machine includes a needle tube which receives a needle which is locked to a frame at a needle retainer. A needle reciprocates within the needle tube and is powered by armature coils which impart vibratory motion to an armature bar attached to the upper end of the needle.

A continuing problem with tattoo machines of this type is that the needle tube is locked to the needle retainer by means of a threaded fastener which is received within a threaded bore at the needle tube retainer. If, due to repeated use, the threads of the needle retainer become stripped or worn, or the needle retainer becomes damaged, conventional practice has been to replace the entire tattoo machine frame. This is an unnecessary wasteful and expensive practice. Accordingly there exists a need for a simple and effective locking device that can be used to secure the needle tube in place even in the event the needle retainer is damaged.

BRIEF SUMMARY OF THE INVENTION

Briefly, the present invention provides a locking device for the needle tube of a tattoo machine. The locking device has an arm with an aperture which receives the needle tube. A locking arm extends at right angles from the needle tube arm and defines a threaded bore which receives a threaded fastener having a knurled outer end. The locking device can be rotated about the needle retainer to desired locking position and the screw tightened to secure the needle tube in place even if the selected position is displaced from the threaded bore in the needle retainer. The needle tube locking device may be sterilized such as by sterilization in an autoclave and will fit most conventional tattoo machines.

BRIEF DESCRIPTION OF THE DRAWINGS

The above invention will be more fully understood from the following descriptions and drawings in which.

DETAILED DESCRIPTION OF THE DRAWINGS

Figure 1:
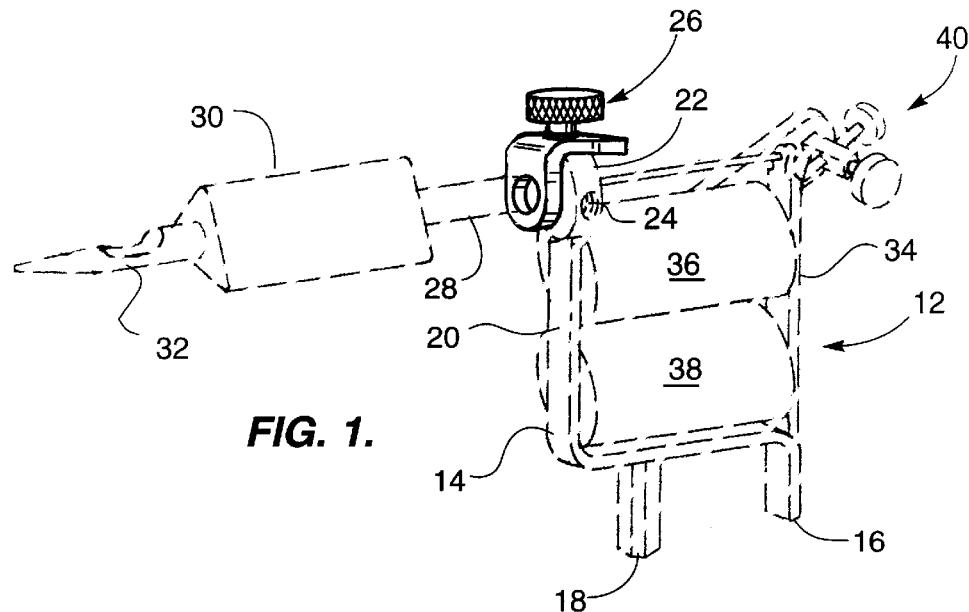
FIG. 1 is perspective view showing a representative tattoo machine with the needle tube lock of the present invention secured thereto.
Figure 2:
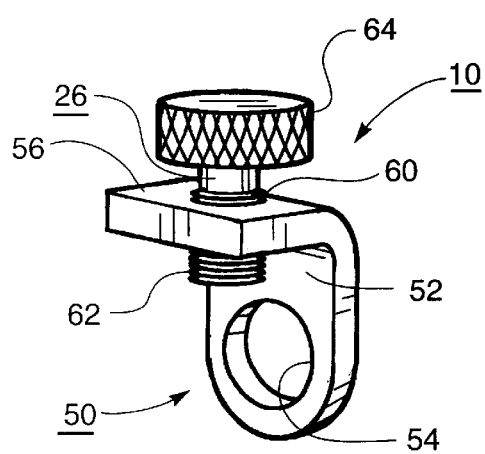
FIG. 2 is perspective view of the needle tube lock of the present invention.

FIG. 1 shows the lock of the present invention which is designated by the numeral 10 in conjunction with a conventional tattoo machine which is shown in dotted lines and represented by the numeral 12.

The tattoo machine 12 is a representative tattoo machine of the type that can be purchased from Superior Tattoo Equipment of Phoenix, Ariz., under the trademark "Black Widow," "Roadrunner" or "Stainless J." Such tattoo machines 12 have a frame 14 which includes a pair of contacts 16 and 18 for attachment to a source of power such as 6V DC. The frame 14 has a lower arm 20 which terminates at a forward end at an annular needle retainer 22. The needle retainer has a radial bore 24 which receives a knurled threaded screw member such as member 26. The knurled threaded screw member 26 engages the exterior of the needle tube 28 to secure it in place. The needle tube 28 carries a grip 30 which is shown as being generally triangular which is grasped by the user during the tattooing procedure. A needle 32 is reciprocal within the needle tube and is used to apply ink to the individual. The upper end of the needle is secured to the armature bar 34 and the coils 36, 38 impart vibratory motion to the armature bar and to the needle. The stroke of the needle can be adjusted by an adjustment mechanism 40.

The above is a general description and is representative of most tattoo machines. A problem exists in that the needle retainer 22 has a threaded bore 24 which, over prolonged use, may become damaged. The threads become worn and are no longer able to accept the needle tube retainer screw 26.

Figure 3:
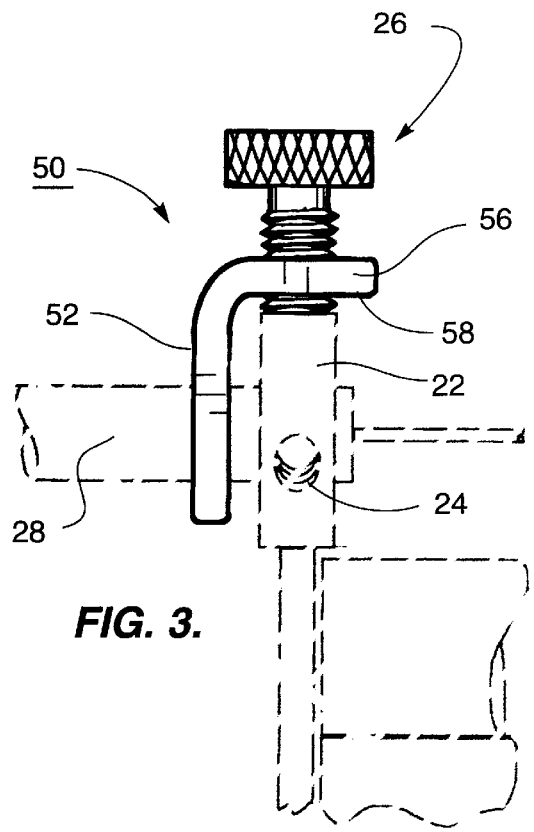
FIG. 3 is a detail view showing the needle tube lock attached about the needle tube and in threaded engagement with the needle retainer.

Accordingly, the present invention provides a lock device generally designated by the numeral 50 which is universal and will attach to most types of tattoo machines so it is not necessary to discard or replace the machine in the event the needle retainer 24 becomes worn or damaged. The lock 50 has a first arm 52 which is the needle tube retainer arm. The arm 52 has a bore 54 which is sized to closely correspond to the diameter of the needle tube. Integrally formed with the retainer arm 52 is a clamping arm 56. The clamping arm 56 extends at right angles with respect to the retainer arm 52 and has an inner surface 58 which is adapted to extend parallel with the needle tube as best seen in FIG. 3. A threaded bore 60 is provided in the arm and receives the threaded end 62 of locking screw 26. The outer end of the locking screw 26 is provided with a knurled knob 64 which is convenient for the user to grasp. The threaded end 62 carries threads which are sized to engage bore 24 in the needle retainer.

Referring to FIG. 3, the lock 50 can be easily secured to an existing tattoo machine by placing the needle tube arm 52 over the needle tube 28. The clamping arm 60 is then positioned so that the screw aligns with the periphery of the needle retainer 22. Note the lock can be rotated approximately 180° to any convenient location in which the screw can be tightened into a locking position against the outer periphery of the needle retainer 22. In this position, the needle tube is secured and it is not necessary to engage the locking screw 26 with the damaged threads of the needle retainer. If the threads 24 are undamaged, the screw 26 can be threadably engaged in the threaded bore 24.

Preferably the lock, including the body and the screw, is fabricated from a material such as a high quality stainless steel so that the lock can be sterilized by sterilization such as by autoclave. The threads can typically be 10–32 threads.

It will be apparent that the locking device of the present invention may be provided as an after-market attachment to allow repair and use of the damaged tattoo machines. Alternatively, the locking device can be also provided as an original equipment and component of new machines. It will also be apparent that the lock is universal as it will fit both right-handed and left-handed tattoo machines.

It will be apparent to those skilled in the art to make various changes, alterations and modifications to the locking device described above. To the extent these various changes, alterations and modifications do not depart from the spirit and scope of the appended claims, they are intended to be encompassed therein.

I claim:

1. A needle tube lock for a tattoo machine of the having a frame, a power source, a needle driven by said power source within a needle tube, and a needle tube retainer on said frame extending around said needle tube, said needle tube retainer having an outer peripheral surface, said needle tube lock comprising:

(a) a needle tube arm defining an aperture to receive said needle tube;

(b) a clamp arm integrally formed with said needle tube arm and being at a general right angle with respect to said needle tube arm and positioned to extend adjacent the surface of the said retainer when said needle tube is disposed in said aperture in a use position, said clamp arm defining a threaded bore aligned with the said peripheral surface of said retainer in said use position and rotatably relative thereto; and (c) a threaded fastener engageable in said threaded bore and manually securable at selected positions along said retainer peripheral surface to releasably lock said needle tube to said frame.

2. The lock of claim 1 wherein said lock is stainless steel.

* * * * *